(12) United States Patent
Glithero et al.

(10) Patent No.: US 11,324,924 B2
(45) Date of Patent: May 10, 2022

(54) TUBING MANAGEMENT MEMBERS AND URINE COLLECTION SYSTEMS USING THE SAME

(71) Applicant: C.R. Bard, Inc., Murray Hill, NJ (US)

(72) Inventors: Jason Iain Glithero, McDonough, GA (US); Salvatore Privitera, Mason, OH (US); Oliver Newman, Stone Mountain, GA (US); Tracey E. Knapp, Snellville, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 426 days.

(21) Appl. No.: 15/767,829

(22) PCT Filed: Oct. 14, 2016

(86) PCT No.: PCT/US2016/057005
§ 371 (c)(1),
(2) Date: Apr. 12, 2018

(87) PCT Pub. No.: WO2017/070013
PCT Pub. Date: Apr. 27, 2017

(65) Prior Publication Data
US 2018/0304045 A1    Oct. 25, 2018

Related U.S. Application Data (60) Provisional application No. 62/245,171, filed on Oct. 22, 2015.

(51) Int. Cl.
*A61M 25/02* (2006.01)
*A61M 39/08* (2006.01)
(Continued)

(52) U.S. Cl.
CPC ........... *A61M 25/02* (2013.01); *A61F 5/4404* (2013.01); *A61F 5/451* (2013.01); *A61M 5/1418* (2013.01); *A61M 39/08* (2013.01); *A61B 10/007* (2013.01)

(58) Field of Classification Search
CPC ................ A61M 5/1418; A61M 39/08; A61M 2025/024; A61M 25/02; F16B 2/005
See application file for complete search history.

(56) References Cited

U.S. PATENT DOCUMENTS 3,834,380 A * 9/1974 Boyd .................... A61M 25/02
                                                    604/180
4,027,842 A    6/1977 Mittleman
(Continued)

OTHER PUBLICATIONS

International Search Report and Written Opinion for International Application No. PCT/US2016/057005 dated Jan. 19, 2017.
(Continued)

*Primary Examiner* — Catharine L Anderson
*Assistant Examiner* — Arjuna P Chatrathi
(74) *Attorney, Agent, or Firm* — Dorsey & Whitney LLP (57) ABSTRACT

Embodiments described herein are directed to tubing management members and urine collection systems including such tubing management members. In an embodiment, a tubing management member may be coupled and, in some embodiments, removably coupled to a drainage tube of the urine collection system. The tubing management member may include a plurality of attachment elements for attaching the tubing management member to the drainage tube.

20 Claims, 4 Drawing Sheets

(51) Int. Cl.
*A61F 5/451* (2006.01)
*A61M 5/14* (2006.01)
*A61F 5/44* (2006.01)
*A61B 10/00* (2006.01)

(56) References Cited

U.S. PATENT DOCUMENTS

| | | | | |
|---|---|---|---|---|
| 4,029,103 A | | 6/1977 | McConnell | |
| 4,406,042 A | * | 9/1983 | McPhee | A61M 5/1418 24/129 A |
| 4,447,238 A | * | 5/1984 | Eldridge, Jr. | A61M 25/02 128/DIG. 26 |
| 4,654,026 A | * | 3/1987 | Underwood | A61M 5/1418 128/DIG. 26 |
| 4,707,906 A | * | 11/1987 | Posey | A61G 7/0503 128/DIG. 26 |
| 4,999,885 A | * | 3/1991 | Lee | A61M 5/1418 24/339 |
| 7,624,480 B2 | * | 12/2009 | Coronel | A61M 25/02 128/DIG. 15 |
| 2006/0211994 A1 | * | 9/2006 | Roman | A61M 5/158 604/180 |
| 2009/0211061 A1 | * | 8/2009 | Cianciolo | B65D 63/1072 24/16 PB |
| 2010/0121288 A1 | | 5/2010 | Timmons | |
| 2010/0286667 A1 | * | 11/2010 | Paz | A61M 1/69 604/544 |
| 2011/0087181 A1 | | 4/2011 | Bidwell et al. | |
| 2014/0074036 A1 | * | 3/2014 | Cheng | A61M 25/02 604/179 |
| 2014/0252177 A1 | | 9/2014 | Vera et al. | |

OTHER PUBLICATIONS

U.S. Appl. No. 62/245,171, filed Oct. 22, 2015.

\* cited by examiner

TUBING MANAGEMENT MEMBERS AND URINE COLLECTION SYSTEMS USING THE SAME

CROSS-REFERENCE TO RELATED APPLICATIONS

This application claims priority to U.S. Provisional Application No. 62/245,171 filed on Oct. 22, 2015, the disclosure of which is incorporated herein, in its entirety, by this reference.

BACKGROUND

Generally, urinary catheterization involves insertion of a urinary catheter through a patient's urethra into a bladder. The urinary catheter (e.g., a Foley urinary catheter) allows the patient's urine to drain from the bladder through a drainage tube into a drainage bag (also referred to as collection bag). The drainage tube may be several feet long. Tubing management systems to stabilize or arrange the drainage tube in a particular manner and/or secure the drainage tube to furniture or medical equipment during the patient's catheterization may be desirable, e.g., to improve the flow of urine through the drainage tube.

Accordingly, manufacturers and users of catheterization and urine collection systems and methods continue to seek improvements thereto.

SUMMARY

Embodiments disclosed herein relate to catheterization and more specifically to urine collection systems and tubing management components thereof that may facilitate improved tubing management during a patient's catheterization. In an embodiment, a urine collection system may include a collection bag (e.g., a urine collection bag) including an inlet and an outlet, a drainage tube connected to the inlet of the collection bag, and a tubing management member coupled to the drainage tube. The tubing management member may include a strip of material defining a first end and an opposing second end. The tubing management member may further include a first end portion defining a first tube passage at least proximate to the first end of the strip of material and a second end portion defining a second tube passage at least proximate to the second end of the strip of material. Each of the first and second tube passages may be configured to receive a portion of the drainage tube therethrough. Each of the first and second tube passages may have a lateral dimension, and the first and second tube passages may be spaced from one another such that a distance between an edge of the first tube passage and an edge of the second tube passage is greater than the lateral dimension of any of the first or second tube passages. The tubing management member may further include a retention element proximate to one of the first or second tube passages configured to secure the tubing management member to a structure.

According to some embodiments, a tubing management member configured to be coupled to a drainage tube of a urine collection system may include a strip of material defining a first end and an opposing second end, a first end portion defining a first tube passage at least proximate to the first end of the strip, a second end portion defining a second tube passage at least proximate to the second end of the strip, and a retention element proximate to one of the first or second tube passages and configured to secure the tubing management member to a structure. Each of the first and second tube passages may be configured to receive a portion of the drainage tube therethrough. Each of the first and second tube passages may have a lateral dimension, and the first and second tube passages may be spaced from one another such that a distance between an edge of the first tube passage and an edge of the second tube passage is greater than the lateral dimension of any of the first or second tube passages. In some embodiments, one or more of the first or second tube passages may be configured to increase a friction between the drainage tube and the tube passages.

According to some embodiment, a method of using a urine collection system may include providing a tubing management member including a first tube passage and a second tube passage, positioning a first location of a drainage tube through the first tube passage, and positioning a second location of the drainage tube through the second tube passage. The tubing management member may include a strip of material defining a first end and a second end. The tubing management member may also include a first end portion defining the first tube passage at least proximate to the first end of the strip of material and a second end portion defining the second tube passage at least proximate to the second end of the strip of material. A length of the drainage tube between the first location of the drainage tube and the second location of the drainage tube may be greater than a distance between the first tube passage and the second tube passage.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

For better understanding, the like elements have been designated by like reference numbers throughout the various accompanying figures. Understanding that these drawings depict only typical embodiments of the disclosure and are not therefore to be considered to be limiting of its scope, the embodiments of the disclosure will be described and explained with additional specificity and detail through the use of the accompanying drawings in which.

DETAILED DESCRIPTION

Embodiments disclosed herein relate to catheterization and, more specifically, to urine collection systems and tubing management components thereof that may facilitate improved tubing management during a patient's catheterization. A patient may need to be catheterized, during hospitalization or surgery, by inserting a catheter into the patient's urinary track and connecting the catheter to a urine drainage and collection system. Typically, the urine drainage and collection system includes a flexible drainage tube, which is connected to the catheter at one end and connected to a collection bag at another end thereof. The collection bag typically includes an inlet connected to the drainage tube and an outlet, which may be used to drain the collection bag and/or obtain a sample of the patient's urine. Following catheterization, typically the drainage tube is draped over the patient's leg and may be secured to the patent's leg (e.g., using medical adhesive tape). The collection bag is typically secured to the bed (e.g., to the frame of the bed) or to another piece of furniture or medical equipment. For example, the collection bag may be suspended from a stand specific for this purpose or a stand supporting other medical equipment.

Typically, and to improve the flow of fluid through the drainage tube, it may be desirable to arrange the collection bag and/or the drainage tube such that a downward path is created for the fluid from the patient to the collection bag. Often, the length of the tubing is greater than a distance between the patient (e.g., the catheter) and the location where the bag is positioned. To deal with the extra length of tubing, the drainage tube is typically looped or coiled, often resulting in dependent loops of tubing, which may include low spots. A low spot in the tubing may negatively impact the flow of fluid because the fluid (e.g., urine) may be required to flow against gravity to reach the collection bag. In addition, vacuum bubbles may be created in the tubing which may result in reducing or stopping the flow of fluid through the drainage tube.

To deal with dependent loops, the hospital staff may be required to move the bag as far away from the patient as may be needed to maintain the tube free from dependent tubes. This may not be practical as the drainage tube may be several feet long, in some examples 4 feet, or 5 feet or 6 feet long. Furthermore, in the case of vacuum bubbles, the hospital staff may need to forcefully manipulate the tubing to restart or improve the flow of fluid, which may be undesirable as it may disrupt the patient and/or pull on the catheter. In addition, the dependent loop problem may be further exacerbated by the reduced height of recently developed hospital beds, which may be the current trend in industry as aimed to reduce fall-related injuries to patients. In some conventional urine collection systems, a rigid snap-type clip may be used to coil the tube; however such rigid devices may create undesirable anchor points that may pull against the patient when the patient moves or may not fully address the issues of dependent loops. The urine collection systems described herein and tubing management components thereof may provide improved solutions.

FIGS. 1-6 show several embodiments of urine collection systems and components thereof according to embodiments of the present disclosure. Embodiments disclosed herein relate to a urine drainage and collection systems that may reduce the presence of dependent loops in a drainage tube of the system and thus improve the flow of fluid through the drainage tube. For example and referring now to FIG. 1, a urine collection system 100 may include a collection bag 102 including an inlet 110 and an outlet 116. The collection bag 102 may be implemented according to any examples known in the art or later developed. For example, the collection bag 102 may be formed of a flexible, rigid, resilient, or any suitable material or combinations of materials. The collection bag 102 may include front and back panels, which may be bonded together to form a fluid tight container. In an embodiment, the collection bag 102 may include and/or may be formed by three or more panels, or a single body. In any event, the panels of the collection bag 102 may be connected and/or bonded together in a manner that forms or defines an interior space of the collection bag 102, which is adapted to contain a fluid (e.g., urine) therein.

Figure 1:
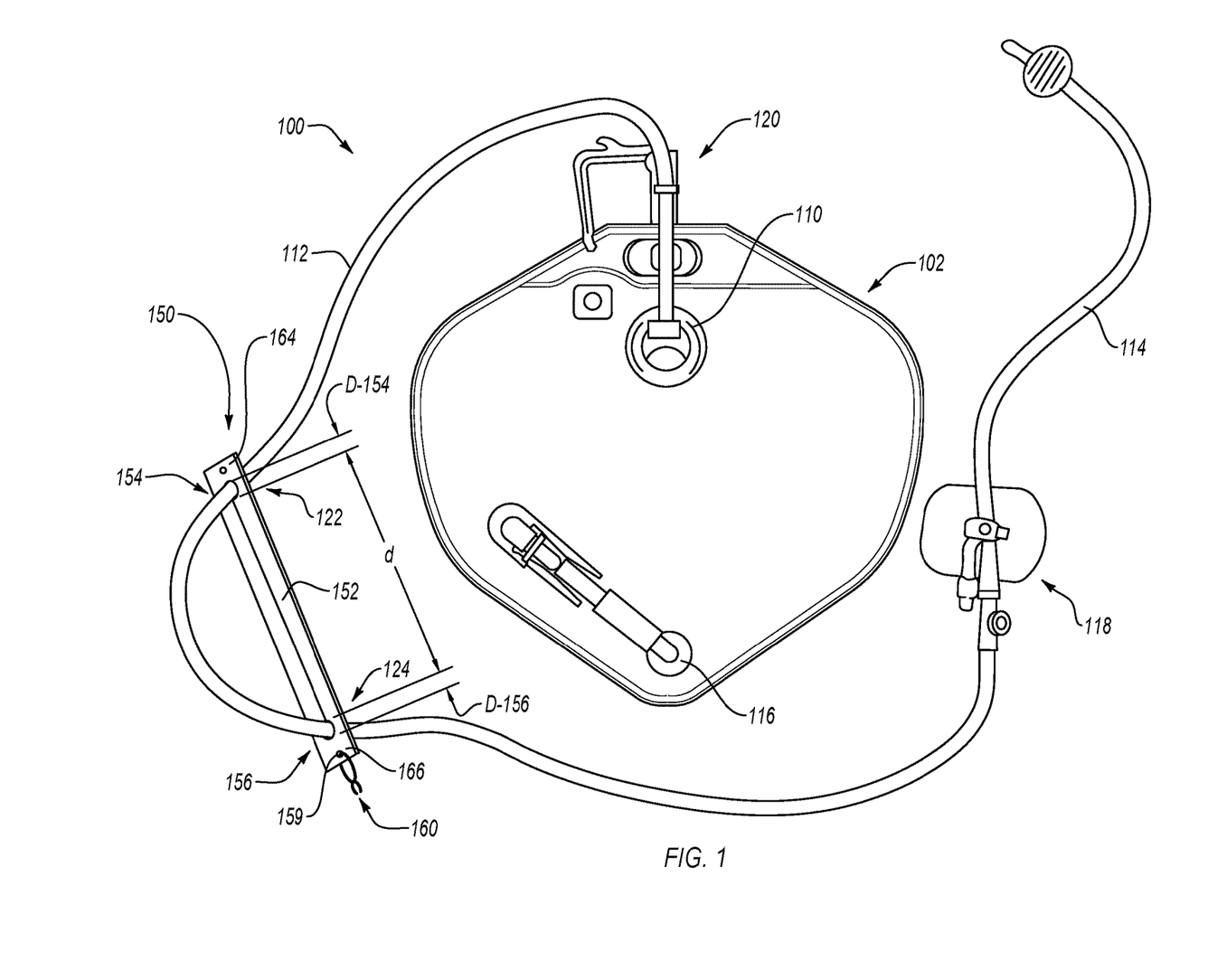
FIG. 1 illustrates a urine collection system including a tubing management member shown in an isometric view, according to an embodiment.

Generally, the collection bag 102 may have any suitable geometry. For example, the collection bag 102 may be generally tear-shaped (as shown in FIG. 1) or it may be generally circular, generally rectangular, oval, or have any irregular shape as may be desired. The inlet 110 of the collection bag 102 may be configured to accept a fluid (e.g. urine) from tubing connected to the collection bag 102. The urine collection system 100 includes a drainage tube 112, which may be connected to the inlet 110 of the collection bag 102. The drainage tube 112 may be in fluid communication with a catheter (e.g., a Foley urinary catheter 114 as in the illustrated example) that may be positioned in a patient's bladder such that urine may flow into the collection bag 102 from the catheter 114 and through the drainage tube 112. The outlet 116 of the collection bag 102 may be located at or along a bottom of the collection bag 102. For example, the outlet 116 may be configured to allow collected urine to flow or drain from the collection bag 102 (e.g., for collecting or extracting urine specimens from the collection bag 102).

The urine collection system 100 further includes a tubing management member 150 coupled to the drainage tube 112. The tubing management member 150 includes a strip 152 of material. In an embodiment, the strip 152 may be a flexible strip formed of a flexible material, such as rubber, silicone, combinations thereof, or any other type of elastomer. In an embodiment, the strip 152 may be a rigid material, such as a thin sheet of rigid plastic, metal, composite material, or combinations thereof. In an embodiment, the strip may include at least one flexible material and at least one rigid material.

In an embodiment, the tubing management member 150 includes a thin piece or sheet of material, such that a thickness of the strip 152 is significantly smaller than, for example, a length of strip 152. In some embodiments, the strip 152 may have a length of about 4 to about 12 inches, such as about 6 to about 10 inches. In some embodiments, the strip 152 may be about 8 inches long. In some embodiments, the strip 152 may have a width of about ½ to about 4 inches, such as about ½ to about 2 inches. In some embodiments, the strip 152 may be about 1 inch wide. In some embodiments, the strip 152 may have a thickness of about 1/16 to about ¼ of an inch. In some embodiments, the strip 152 may be about ⅛ of an inch thick.

The strip 152 includes a first end portion 164 that defines a first tube passage 154 and a second end portion 166 that defines a second tube passage 156. The first tube passage 154 may be located at least proximate to the first end portion 164 of the strip 152 and the second tube passage 156 may be located at least proximate to an opposite second end portion 166 of the strip 152. Each of the first and second tube passages 154, 156 is configured to receive a portion of the drainage tube 112 therethrough. In other words, when tubing management member 150 is coupled to the drainage tube 112, a first location 122 of the drainage tube 112 passes through the first tube passage 154 and a second location 124 of the drainage tube 112 passes through the second tube passage 156. The first and second tube passages 154, 156 may include features configured to increase a friction between the drainage tube 112 and the first and second tube passages 154, 156. For example a size and/or shape of the first and second tube passages 154, 156 may be selected such that static friction is increased. In some embodiments, the first and second tube passages 154, 156 may be sized for an interference fit between the strip 152 and the drainage tube 112.

The first and second tube passages 154, 156 may have a lateral dimension that may be selected to increase a frictional fit between the tube passages and the drainage tube. In some embodiments, the lateral dimension may be a diameter, which may be the same as, slightly larger than, or slightly smaller than a diameter of the tubing to be inserted therethrough. As will be described further below, in some embodiments, a managed bend may be formed in the drainage tube 112 via the use of the tubing management member 150. The managed bend may reduce or eliminate the risk of low spots in the drainage tube 112 and thus may improve flow of urine through the drainage tube 112. The first and second tube passages 154, 156 of the tubing management member 150 may be spaced from one another such that a distance d between a bottom edge of the first tube passage 154 and a top edge of the second tube passage 156 is greater than the respective lateral dimensions D-154, D-156 of the first and second tube passages 154, 156. In this manner, a predetermined spacing may be maintained between portions of the drainage tube 112 that are restrained by the tubing management member 150, such as to form and maintain a managed bend of tubing as described herein.

In an embodiment, the tubing management member 150 may include a strip of flexible material. In such an embodiment, the tubing management member 150 may interchangeably be referred to as a flexible member or flexible strip. As a flexible strip, the tubing management member 150 is capable of being flexed or bent out of plane. In some embodiments, the flexible strip may be stretchable in that it may be capable of elongation along a length of the flexible strip. In an embodiment, the tubing management member 150 may be formed of a rigid material and may not be easily manually bent or stretched.

The tubing management member 150 may be used to reduce a distance between a first end (e.g., catheter end 118) and second end (e.g., bag end 120) of the drainage tube 112 by creating one or more managed bends in the drainage tube 112. The managed bend may include a generally C-shaped or U-shaped (e.g., semi-circular or semi-ovular) curve or loop in the drainage tube 112. The perceived length of the drainage tube 112 between the first end and the second end of the drainage tube 112 is reduced by shaping or looping the drainage tube 112 at one or more intermediate locations (e.g., by forming the one or more managed bends along the length of the drainage tube). As will be appreciated, the tubing management member 150 is coupled to a first location 122 of the drainage tube 112 via the first end portion 164 of the strip 152 and is further coupled to a second location 124 of the drainage tube via the second end portion 166 of the strip 152. The length of drainage tube 112 between the first location 122 and the second location 124 is greater than the length of the strip 152. By restraining two points of the drainage tube 112 along a line via the strip 152, a reduction in the perceived length of the tubing may be achieved. By coupling the tubing management member 150 to the drainage tube 112 in this manner, a managed bend having a generally C-shape or U-shape may be formed.

Notably, a configuration of the curve or loop as may be affected by the tubing management member 150 is selected to avoid low points in the drainage tube 112. For example, the drainage tube 112 may be arranged such that overlapped sections of tubing are avoided. The curvature or shape of the managed bend may be controlled by a length of the tubing management member 150, and particularly by a spacing between the first and second tube passages 154, 156. For example, the first and second tube passages 154, 156 may be spaced from one another by a distance that is greater than a lateral dimension of any of the first or second tube passages 154, 156. In some embodiments, the first and second tube passages 154, 156 may be spaced from one another by a distance that is at least two times the lateral dimension.

The drainage tube 112 may be arranged such that the portion of the drainage tube 112 associated with the managed bend generally lies in a bend plane. In some embodiments, the bend plane may be arranged (e.g., by use of tubing management member 150) generally parallel to the ground or at an incline with the ground wherein an elevated end of the bend plane corresponds to an upstream location of the drainage tube 112 and a lowered end of the bend plane corresponds to a downstream location of the drainage tube. The bend plane may be maintained in a generally parallel orientation with respect to the ground, such as by positioning the tubing management member 150 such that it lies flat on a surface that is also generally parallel with the ground (e.g., the patient's bed). Because the tubing management member 150 secures two points of tubing arranged generally in a line, the portion of drainage tube 112 between these two points may thus be arranged in a bend plane that is maintained generally parallel with the ground and, thus, low spots in the tubing are avoided.

In some embodiments, the tubing management member 150 of the urine collection system 100 may include a retention element proximate to one of the first or second tube passages 154, 156. The retention element may be configured to secure the tubing management member 150 to another structure e.g., a bed sheet, furniture (e.g., the bed frame), or equipment. In some embodiments, the strip 152 may define at least one securing hole 159 and the retention element may include at least one clip 160. In such embodiments, the clip 160 may be attached to the rest of the tubing management member 150 via the securing hole 159. The clip 160 may be used to stabilize the tubing, such as by securing the rest of the tubing management member 150 to another structure (e.g., a bed sheet).

The clip 160 may be coupled proximate to one end of the tubing management member 150. That is, the clip 160 may be coupled to the first end portion 164 or the second end portion 166 of the strip 152. The clip 160 may be coupled to the end portion of the strip 152 that is engaged with an upstream portion (e.g., second location 124) of the drainage tube 112, while the other end portion of the strip 152 is engaged with a downstream portion (e.g., first location 122) of the drainage tube 112. The terms upstream and downstream, in the context of this disclosure, imply relative locations with respect to a flow of fluid through the tubing. For example, by upstream, it is implied that a certain volume of urine would pass through the upstream portion of the tubing before it passes through the downstream portion of the tubing. As will be appreciated, by securing, e.g., via the clip 160, an upstream location of the drainage tube 112 to another structure, the bend plane of the managed bend of the drainage tube 112 may be maintained in a generally parallel orientation or in an inclined orientation with the upstream portion above the downstream portion, even if an unsecured portion of the tubing (e.g., downstream location) becomes unsupported and/or drops towards the ground under the force of gravity. In this manner, low spots in the tubing may be avoided or eliminated and the flow of urine through the drainage tube 112 may be improved.

Figure 2:
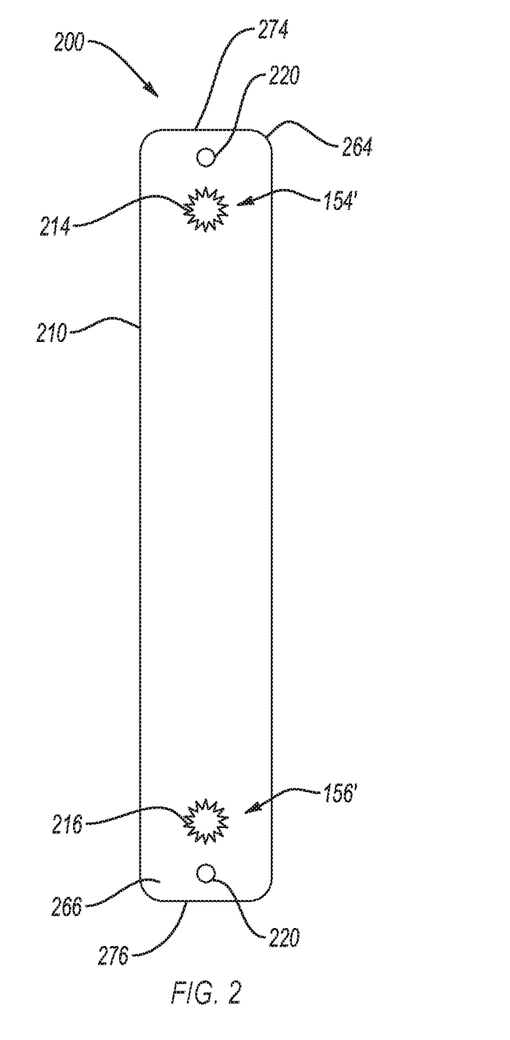
FIG. 2 is a plan view of a tubing management member for a urine collection system according to an embodiment.

With reference now also to FIG. 2, an embodiment of a tubing management member 200 is described. Except as otherwise described herein, the tubing management member 200 and its materials, components, or elements can be similar to or the same as the tubing management member 150 (FIG. 1) and its respective materials, components, or elements. The tubing management member 200 or its materials, components, or elements can be used in any of the tubing management members or systems disclosed herein.

The tubing management member 200 includes a strip 210 of material. The strip 210 may include a plurality of holes through a thickness of the strip 210. The plurality of holes includes a first tube hole 214 in a first end portion 264 of the strip 210 and a second tube hole 216 in a second end portion 266 of the strip 210. The first tube hole 214 defines the first tube passage 154' and the second tube hole 216 defines the second tube passage 156'. The first and second tube holes 214, 216 may be configured for insertion of the drainage tube therethrough (e.g., as shown in FIG. 1). For example, the first and second tube holes 214, 216 may be shaped to accommodate passage of the drainage tube through the first and second tube holes 214, 216. The first and second tube holes 214, 216 may have a relevant size (e.g., a radius or a diameter) that may be the same as, slightly smaller than, or slightly larger than a relevant size (e.g., radius or a diameter) of the drainage tube. The first and second tube holes 214, 216 may have a circular shape, which may correspond with a cross-sectional shape of the drainage tube. In some embodiments, the diameter of the tube hole may be larger than a diameter of the tubing.

In some embodiments, the first and second tube holes 214, 216 may include features configured to increase the friction between the drainage tube and the tubing management member 200. For example, a shape of the tube hole (e.g., hole geometry) may be selected such that an edge of the hole is, at least partially, in contact with the drainage tube. In some embodiments, one or more of the tube holes may have a rectangular, square, triangular, trapezoidal, oval, or star shape or any combinations thereof. In some embodiments, one or more of the first and second tube holes 214, 216 may have an irregular shape. In the embodiment in FIG. 2, the first and second tube holes 214, 216 are star-shaped tube holes. The star-shaped tube holes may include edge features which extend radially inward to engage the drainage tube. An outer diameter of the star-shaped tube hole may be greater than the diameter of the tubing and an inner diameter of the star-shaped tube hole may be smaller than the diameter of the tubing. In this manner, at least part of the star-shaped tube hole engages the drainage tube when inserted therethrough to increase friction and prevent the drainage tube from freely sliding within the first and second tube holes 214, 216. A tubing management member as described herein may accommodate drainage tubes having different diameters, e.g., up to a diameter substantially equal to the outer diameter of the star-shaped tube holes. Other hole geometries may be used in other embodiments.

In some embodiments, the strip 210 may include one or more securing holes 220 in one or more of the first or second end portions 264, 266. In the embodiment shown in FIG. 2, the strip 210 includes two securing holes 220 substantially symmetrically arranged proximate to opposite ends of the strip 210. Each of the securing holes 220 in the embodiment shown in FIG. 2 are located between an edge (e.g., first edge 274, second edge 276) of the strip 210 and the respective tube hole (e.g., first tube hole 214, second tube hole 216) located proximate to the corresponding one of the first edge 274 or the second edge 276. The tubing management member 200 may include a at least one retention element (not shown), such as at least one clip, configured to secure the tubing management member 200 to a structure (e.g., a bed sheet).

Figure 4A:
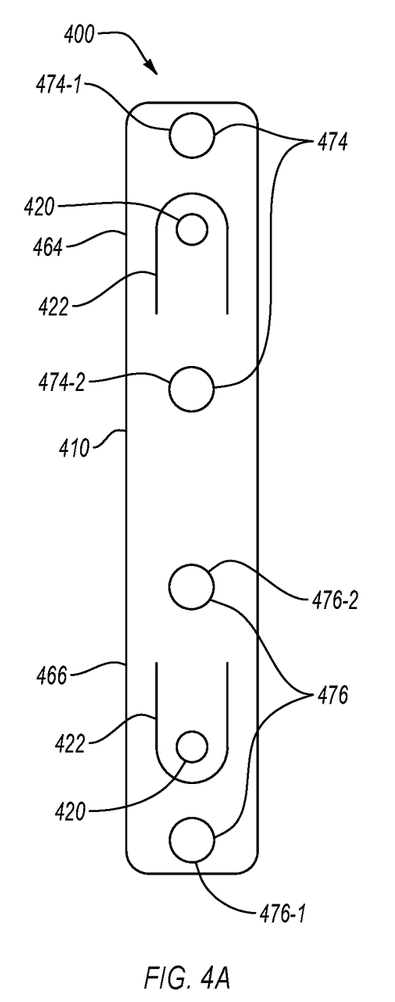
FIG. 4A is a plan view of a tubing management member for a urine collection system according to a further embodiment.

In the embodiment in FIG. 2, when the strip 210 is coupled to the drainage tube, a bend plane of a managed bend of the drainage tube and the plane of the strip 210 are generally perpendicularly aligned by virtue of the drainage tube passing through the first and second tube holes 214, 216 and through the plane of the strip 210. In further embodiments, as will be described with reference to FIGS. 4 and 5, a bend plane of a managed bend of the drainage tube and a plane of a strip forming a tubing management member may be generally parallel to one another. In some embodiments, the tubing management member 200 may be coupled to the drainage tube (e.g., the drainage tube may be passed through each of the first and second tube holes 214, 216) prior to connecting the drainage tube to the patient, for example, during manufacture of the urine collection system.

Figure 3:
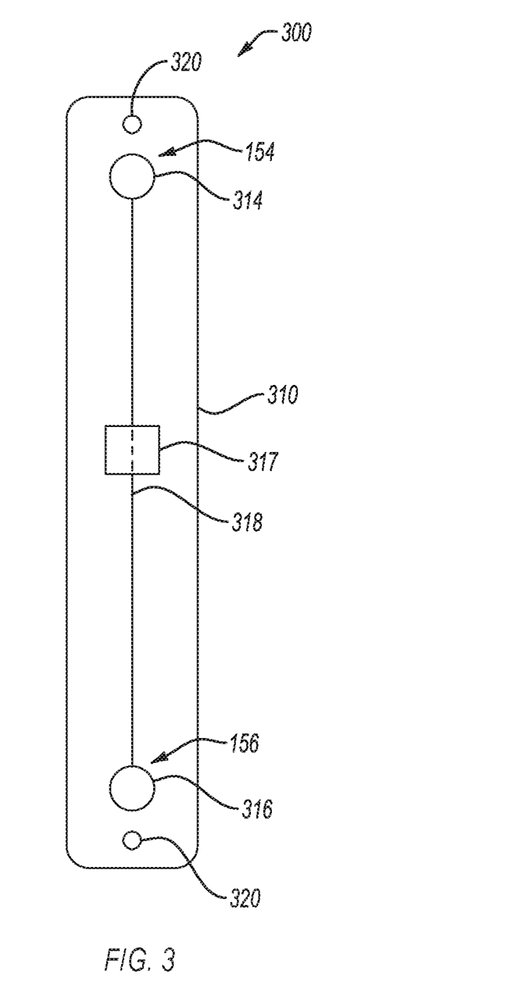
FIG. 3 is a plan view of a tubing management member for a urine collection system according to yet another embodiment.

In some instances, a tubing management member may be coupled to a drainage tube after a catheter and the drainage tube are connected to the patient, such as when a urine collection system does not include a tubing management member and/or in the event that the tubing management member included with the urine collection system becomes damaged or unusable during the period of catheterization. Referring now to FIG. 3, an embodiment of a tubing management member 300 is described, which is configured to be coupled to a drainage tube after a catheter and the drainage tube are connected to a patient. Except as otherwise described herein, the tubing management member 300 and its materials, components, or elements can be similar to or the same as the tubing management member 150, 200 (FIGS. 1-2) and their respective materials, components, or elements. For example, the tubing management member 300 may include a strip 310 of material. The tubing management member 300 or its materials, components, or elements can be used in any of the tubing management members or systems disclosed herein.

The strip 310 of the tubing management member 300 may have a length that is greater than a width thereof which is greater than a thickness thereof. The strip 310 may include a plurality of holes for coupling the strip 310 to a drainage tube of a urine collection system. For example, the strip 310 may include a first end portion including a first tube hole 314 that defines the first tube passage 154 and a second end portion comprising a second tube hole 316 which defines the second tube passage 156. The first and second tube holes 314, 316 may be configured for insertion of the drainage tube 112 therethrough (e.g., as illustrated in FIG. 1). In some embodiments, the first and second tube holes 314, 316 may have one or more of the features of the first and second tube holes 214, 216 described above. For example, individual ones of the first and second tube holes 314, 316 may include features (e.g., hole geometries) configured to increase the friction between the tube hole and the drainage tube passing through the tube hole. The shape of the tube hole may be selected, as an example, from a square shape, a rectangular shape, a star shape, or any other irregular shape. The tubing management member 300 may also include one or more securing holes 320 that may be the same or similar to the securing holes 220 of tubing management member 200. In some embodiments, the tubing management member 300 may include at least one retention element (not shown), such as at least one clip, which may be coupled to the tubing management member 300 via one of the securing holes 320.

In the embodiment in FIG. 3, the tubing management member 300 may be configured to enable attachment or removal of the tubing management member 300 to drainage tube (not shown) after the drainage tube is connected (e.g., via the catheter 114 shown in FIG. 1) to a patient. That is, the tubing management member 300 may be configured such that the tubing management member 300 may be attachable to or removable from the drainage tube during the period of catheterization, such as without requiring removal of the drainage tube from the patient. In the embodiment in FIG. 3, the strip 310 defines a slit 318 connecting the first tube hole 314 and the second tube hole 316. In other words, the slit 316 may extend along a length of the strip 310, spanning a distance between the first tube hole 314 and the second tube hole 316. The slit 318 may accommodate attachment and/or removal of the tubing management member 300 to and from the drainage tube without disconnecting the drainage tube from the patient and/or the collection bag 102. The tubing management member 300 may be attached to the drainage tube by passing a portion of the drainage tube (e.g., a managed bend) through slit 318. The drainage tube may be moved into position until the first and second tube holes 314 and 316 engage the drainage tube. Thus, the slit 316 is a through opening that extends completely through a thickness of the strip 310.

In some embodiments, the tubing management member 300 may include a closure mechanism (e.g., a slit fastener 317) associated with the slit 318, which may be configured to reattach opposing sides of the slit 318 (obscured portions of the slit 318 are shown using phantom lines) after the tubing management member 300 is installed on the drainage tube. The slit fastener 317 may be any type of fastener or closure mechanism known or later developed. For example, the slit fastener 317 may be a snap type fastener, a hook-and-loop fastener, a hook and eye closure, an adhesive closure, or combinations thereof. The slit fastener 317 may be located anywhere along the length of the slit 318. The slit fastener 317 may secure or connect opposing sides of the slit 318 at one (as shown) or multiple locations along the slit 318, or along the full or substantially full length of the slit 318.

Figure 4B:
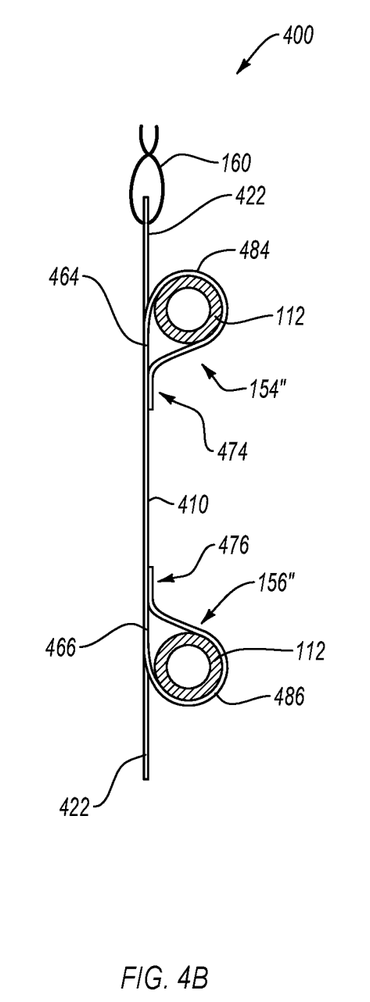
FIG. 4B is a side view of the tubing management member shown in FIG. 4A.

Referring now to FIGS. 4A and 4B, another embodiment of a tubing management member 400 is described. Except as otherwise described herein, the tubing management member 400 and its materials, components, or elements can be similar to or the same as the tubing management member 150, 200, 300 (FIGS. 1-3) and their respective materials, components, or elements. For example, the tubing management member 400 includes a strip 410 of material. The strip 410 may include a first end portion 464 and a second end portion 466 which are configured to define first and second tube passages 154", 156". The tubing management member 400 or its materials, components, or elements can be used in any of the tubing management members or systems disclosed herein.

The strip 410 may include a first fastener 474 located on the first end portion 464 of the strip 410 and a second fastener 476 located on the second end portion 466 of the strip 410. The first and second end portions 464, 466 are configured to wrap around a portion of the drainage tube 112. The fasteners 474, 476 may include virtually any suitable mechanical fastener, such as a snap type fastener, a hook-and-loop fastener, a hook and eye closure, an adhesive closure, or combinations thereof. The fasteners 474, 476 are configured to connect to opposite ends of the first and second end portions 464, 466 to form first and second loops 484, 486, respectively. For example, the first fastener 474 may include a first fastener portion 474-1, such as a male portion of a snap button, that is connected to one end of the first end portion 464 and a second fastener portion 474-2, such as the female portion of the snap button, that is connected to the opposite end of the first end portion 464. The first and second fastener portions 474-1 and 474-2 may snap together to join the opposite ends of the first end portion 464 to thereby define the first loop 484. Similarly, the second fastener 476 may include a first fastener portion 476-1, such as a male portion of a snap button, that is connected to one end of the second end portion 466 and a second fastener portion 476-2, such as the female portion of the snap button, that is connected to the opposite end of the first end portion 466. The first and second fastener portions 476-1 and 476-2 may snap together to join the opposite ends of the second end portion 466 to thereby define the second loop 486. In this embodiment, the first loop 484 defines the first tube passage 154" and the second loop 486 defines the second tube passage 156". As will be appreciated, the first loop 484 has a central axis (also referred to as first loop central axis) which is aligned or parallel to the longitudinal axis of the drainage tube 112, shown in cross section in FIG. 4B. The second loop 486 has a central axis (also referred to as second loop central axis), which is also substantially aligned or parallel to the longitudinal axis of the drainage tube 112. The central axes of the first and second loops 484, 486 are thus substantially aligned or parallel to the bend plane defined by the managed bend of the drainage tube 112. The plane of the strip 410 is generally parallel to the bend plane defined by the managed bend of the drainage tube 112.

The tubing management member 400 may include one or more securing holes 420 configured to attach at least one retention element thereto. For example, the retention element may include at least one clip 160 attached to at least one of the one or more securing holes 420. In some embodiments, a pair of securing holes may be included, and each securing hole 420 of the pair may be located near opposite ends of the tubing management member 400. The one or more securing holes 420 may be configured such that a clip 160 may be interchangeably attached to either end of the tubing management member 400. While clip 160 is illustrated (in FIG. 4B) attached to tubing management member 400 near the first end portion 464, it will be understood that the clip 160 may, in some examples, be attached to tubing management member 400 near the second end portion 466. In some examples, the tubing management member 400 may include two clips 160, each located at respective first and second end portions 464, 466. The securing hole(s) 420 may be provided on tabs 422, which are positioned between ends of the first and second end portions 464, 466 of the strip 410. That is, a securing hole 420 may be located between first fastener portions 474-1, 476-1 and second fastener portions 474-2, 476-2 of the first and second fasteners 474, 476, respectively. In some embodiments, the tab 422 may be positioned midway between the fastener portions such that the tab 422 extends outward from the first and second loops 484, 486 and/or is generally aligned in a plane with the plane of the strip 410 when the first and second tube passages 154", 156" are defined.

Figure 5:
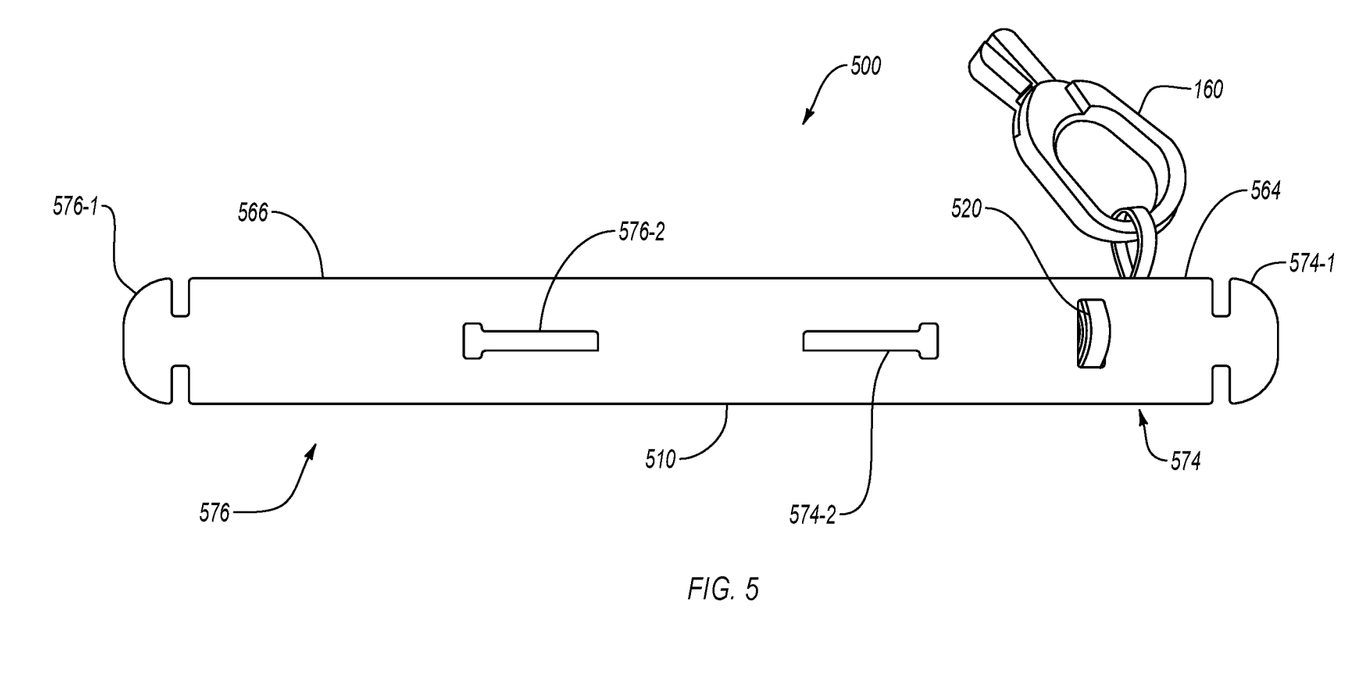
FIG. 5 is a plan view of a tubing management member for a urine collection system according to an embodiment.

Referring now to FIG. 5, yet another embodiment of a tubing management member 500 is described. Except as otherwise described herein, the tubing management member 500 and its materials, components, or elements can be similar to or the same as the tubing management member 150, 200, 300, 400 (FIGS. 1-4) and their respective materials, components, or elements. For example, the tubing management member 500 may include a strip 510 of material. The strip 510 may include a first end portion 564 and a second end portion 566 which are configured to define the first and second tube passages. The tubing management member 500 or its materials, components, or elements can be used in any of the tubing management members or systems disclosed herein.

Similar to the embodiment in FIG. 4, the strip 510 may include a first fastener 574 located on the first end portion 564 of the strip 510 and a second fastener 576 located on the second end portion 566 of the strip 510. The first and second end portions 564, 566 are configured to wrap around a portion of the drainage tube (not shown). The fasteners 574, 576 in the embodiment in FIG. 5 are implemented as tab and slot fasteners. For example, each of the first and second fasteners 574, 576 includes an ear tab 574-1, 576-1 and a slot 574-2, 576-2 configured to receive a respective one of the ear tabs 574-1, 576-1. The ear tabs 574-1, 576-1 are configured to be inserted into a respective one of the slots 574-2, 576-2 to connect respective ends of the first and second end portions 564, 566 thereby forming the first and second loops, respectively, and defining the first and second tube passages, respectively. The drainage tube passes through the first loop and second loops in a similar manner as shown in the example in FIG. 4B. Similar to the embodiment in FIG. 4B, the first and second loops formed by the tab and slot fasteners in this embodiment have central axes that are generally parallel to a plane of the strip 510 and generally parallel to a bend plane defined by the managed bend of the drainage tube.

As in other embodiments, the tubing management member 500 may include one or more securing holes 520 and/or at least one retention element (e.g., at least one clip 160) attached thereto. The securing holes 520 may be provided in one or both of the end portions 564, 566 of the tubing management member 500 for securing a clip 160 to either or both of the end portions 564, 566 of the tubing management member 500. In some examples, the tubing management member 500 may include a pair of securing holes 520 and/or a pair of clips 160, each attached to the tubing management member 500 via respective ones of the securing holes 520.

The tubing management member may be manufactured, such as by laser cutting or stamping the strip (e.g., the strip 210, 310, 410, 510) from a thin sheet of material. In some embodiments and for ease of manufacturing, the tubing management member (e.g., tubing management members 200, 300, 400, 500) may include a pair of opposing and symmetric securing holes although in examples only one securing hole may be needed during use, e.g., for attaching the tubing management member 500 to other structure and thereby stabilizing the portion of tubing with which the tubing management member 500 is engaged. It will be understood that urine collection systems according to embodiments of the present disclosure may include a tubing management member 150 that may be implemented according to any of the embodiments described herein (e.g., tubing management members 200, 300, 400, and 500). In addition certain features of the tubing management members may be used in combination with any of the examples of tubing management members described herein even if not specifically illustrated in that combination. It will be further appreciated, that although the drainage bags described above has been discussed in the context of urinary drainage systems, in other embodiments of the invention, the drainage bags disclosed herein are not limited to such use and may be used for other applications.

Although the present invention has been disclosed and described by way of some embodiments, it is apparent to those skilled in the art that several modifications to the described embodiments, as well as other embodiments of the present invention are possible without departing from the spirit and scope of the present invention.

What is claimed is:

1. A tubing management member configured to be coupled to a drainage tube of a urine collection system, the tubing management member comprising:
   a strip of material defining a top exterior surface, an opposite bottom exterior surface, a first end, and an opposing second end, the strip of material including a plurality of holes through a thickness thereof including a first tube hole and a second tube hole defining a first tube passage and a second tube passage, respectively, the strip of material including a slit connecting the first and second tube holes, the slit spaced from edges of the strip of material;
   a first end portion defining the first tube passage at least proximate to the first end of the strip;
   a second end portion defining the second tube passage at least proximate to the second end of the strip;
   wherein each of the first and second tube passages is configured to receive a portion of the drainage tube therethrough, each of the first and second tube passages having a lateral dimension, the first and second tube passages spaced from one another such that a distance between an edge of the first tube passage and an edge of the second tube passage is greater than the lateral dimension of any of the first or second tube passages, and one or more of the first or second tube passages configured to increase a friction between the drainage tube and the tube passages; and
   a retention element proximate to one of the first or second tube passages and configured to secure the tubing management member to a structure.

2. The tubing management member of claim 1, wherein the strip of material includes a flexible strip formed of an elastomer material, the flexible strip including the first and second end portions.

3. The tubing management member of claim 1, wherein the strip of material includes a rigid material.

4. The tubing management member of claim 1, further comprising a slit fastener configured to reattach sides of the slit together.

5. The tubing management member of claim 1, wherein the strip of material defines one or more securing holes and the retention element is coupled to at least one of the one or more securing holes.

6. The tubing management member of claim 5, wherein the strip of material includes at least one tab and at least one of the one or more securing holes is located on the at least one tab.

7. The tubing management member of claim 5, wherein the retention element includes a clip.

8. A urine collection system, comprising:
   a collection bag including an inlet and an outlet;
   a drainage tube connected to the inlet of the collection bag; and
   a tubing management member coupled to the drainage tube, the tubing management member including:
   a strip of material defining a top exterior surface, an opposite bottom exterior surface, a first end, and an opposing second end, the strip of material including a plurality of holes through a thickness thereof including a first tube hole and a second tube hole defining a first tube passageway and a second tube passage, respectively, the strip of material including a slit connecting the first and second tube holes, the slit spaced from edges of the strip of material;

a first end portion defining a first tube passage at least proximate to the first end of the strip of material and a second end portion defining a second tube passage at least proximate to the second end of the strip of material, wherein each of the first and second tube passages are configured to receive a portion of the drainage tube therethrough, each of the first and second tube passages having a lateral dimension, the first and second tube passages spaced from one another such that a distance between an edge of the first tube passage and an edge of the second tube passage is greater than the lateral dimension of any of the first or second tube passages; and a retention element proximate to one of the first or second tube passages and configured to secure the tubing management member to a structure.

9. The urine collection system of claim 8, wherein the strip of material includes a flexible material.

10. The urine collection system of claim 8, further comprising a slit fastener configured to reattach side of the slit together.

11. The urine collection system of claim 8, wherein at least one of the first tube hole or the second tube hole includes a hole geometry selected to increase friction between the strip of material and the drainage tube.

12. The urine collection system of claim 8, wherein at least one of the first tube hole or the second tube hole has a rectangular, square, triangular, trapezoidal, or star shape.

13. The urine collection system of claim 8, wherein at least one of the first tube hole or the second tube hole has an irregular shape.

14. The urine collection system of claim 8, wherein the tubing management member is removable from the drainage tube during a period of catheterization of a patient.

15. The urine collection system of claim 8, wherein the strip of material defines a pair of securing holes arranged substantially symmetrically at opposite ends of the strip of material, the tubing management member further including a clip coupled to the strip of material via one of the pair of securing holes.

16. A method of using a urine collection system, the method comprising:
providing a tubing management member including:
a strip of material defining a top exterior surface, an opposite bottom exterior surface, a first end, and an second end, the strip of material including a plurality of holes through a thickness thereof including a first tube hole and a second tube hole defining a first tube passageway and a second tube passage, respectively, the strip of material including a slit connecting the first and second tube holes, the slit spaced from edges of the strip of material;
a first end portion defining a first tube passage at least proximate to the first end of the strip of material and a second end portion defining a second tube passage at least proximate to the second end of the strip of material;
passing a portion of a drainage tube through the slit;
positioning a first location of the drainage tube through the first tube passage; and
positioning a second location of the drainage tube through the second tube passage;
wherein a length of the drainage tube between the first location of the drainage tube and the second location of the drainage tube is greater than a distance between the first tube passage and the second tube passage.

17. The method of claim 16, further comprising:
attaching a bag end of the drainage tube to an input of a drainage bag; and
attaching a catheter end of the drainage tube to a catheter.

18. The method of claim 17, wherein the acts of positioning a first location of a drainage tube through the first tube passage and positioning a second location of the drainage tube through the second tube passage are performed prior to the acts of attaching a bag end of the drainage tube to an input of a drainage bag and attaching a catheter end of the drainage tube to a catheter.

19. The method of claim 17, wherein the acts of positioning a first location of a drainage tube through the first tube passage and positioning a second location of the drainage tube through the second tube passage are performed after the acts of attaching a bag end of the drainage tube to an input of a drainage bag and attaching a catheter end of the drainage tube to a catheter.

20. The method of claim 16, further comprising
passing a portion of the drainage tube through the slit.

* * * * *